United States Patent [19]
Lindenman et al.

[11] Patent Number: 5,623,924
[45] Date of Patent: Apr. 29, 1997

[54] APPARATUS AND METHOD FOR RETAINING AN ENDOTRACHEAL TUBE

[76] Inventors: Tammy S. Lindenman, 1917 Washington La., Bensalem, Pa. 19020; Kathryn E. Aubry, 1731 Lansing, Philadelphia, Pa. 19111

[21] Appl. No.: 625,626

[22] Filed: Mar. 29, 1996

[51] Int. Cl.$^6$ .................................................. A61M 16/04
[52] U.S. Cl. .................. 128/207.17; 128/DIG. 15; 128/200.26; 128/207.18; 24/442; 24/306
[58] Field of Search ...................... 128/DIG. 26, 207.14, 128/207.17, 207.18, 911, 912, DIG. 15, 200.26; 604/77, 78, 79, 117, 264, 174, 177, 178, 179; 24/442, 306

[56] References Cited

U.S. PATENT DOCUMENTS

| | | | |
|---|---|---|---|
| 3,288,136 | 11/1966 | Lund | 128/207.17 |
| 4,548,200 | 10/1985 | Wapner | 128/207.17 |
| 4,844,061 | 7/1989 | Carrol . | |
| 5,076,269 | 12/1991 | Austin . | |
| 5,205,832 | 4/1993 | Tuman . | |
| 5,345,931 | 9/1994 | Battaglia . | |
| 5,398,679 | 3/1995 | Freed . | |
| 5,402,776 | 4/1995 | Islava . | |
| 5,411,484 | 5/1995 | Shattuck | 128/207.17 |
| 5,421,327 | 6/1995 | Flynn . | |

*Primary Examiner*—Jennifer Bahr
*Assistant Examiner*—Robert N. Wieland
*Attorney, Agent, or Firm*—LaMorte & Associates

[57] ABSTRACT

A device and associated method for retaining an endotracheal tube in a set position during a period of intubation. The device includes a tubular element that extends at least partially into the mouth of the patient being intubated. The tubular element has an interior surface upon which is affixed a first piece of hook and loop fastening material. A second piece of hook and loop fastening material is affixed to the endotracheal tube to be used during intubation. The endotracheal tube is advanced into the patient through the center of the tubular element. As the hook and loop material on the endotracheal tube advances into the tubular element, an interference fit occurs between the hook and loop fastening material on the endotracheal tube and the hook and loop fastening material lining the tubular element. As the two section of hook and loop fastening material engage one another, the two sections adhere to one another, thereby connecting the endotracheal tube to the tubular element.

12 Claims, 3 Drawing Sheets

APPARATUS AND METHOD FOR RETAINING AN ENDOTRACHEAL TUBE

BACKGROUND OF THE INVENTION

1. Field of the Invention

The present invention relates to endotracheal tube holder devices and methods for retaining an endotracheal tube in a set position after a patient is intubated. More particularly, the present invention relates to endotracheal tube holders that strap to the head of an intubated patient and physically engage the endotracheal tube, thereby retaining the endotracheal tube in one position.

2. Prior Art Description

To properly perform an endotracheal intubation procedure, the distal end of an endotracheal tube must be positioned within a patient's trachea. The trachea is the region of the throat that lays between the larynx and the left and right bronchi of the lungs. During the entire intubation period, the distal end of the endotracheal tube must be retained within the confines of the trachea. If the distal end of an endotracheal tube were to move out of the trachea, above the larynx, the vocal cords may close, preventing the intubation of the lungs. This can cause suffocation. If the vocal cords do not close gastric content aspiration could occur.

If the distal end of the endotracheal tube descends below the trachea, the endotracheal tube typically enters the right mainstream bronchus of the lung. Accidental right mainstream endotracheal intubation is a common cause of pulmonary morbidity (e.g. lung collapse, hypoxemia, cardiac arrest, etc.) in all patients undergoing an endotracheal intubation procedure. Accidental right mainstream endotracheal intubation occurs when an endotracheal tube is advanced too far within a patient's trachea. In such a situation, the endotracheal tube enters the right bronchus of the lung causing the left lung to collapse. Such accidental right mainstream endotracheal intubation results in many deaths each year and causes surviving patients to require extensive pulmonary care.

In the prior art, there exist many features designed into endotracheal tubes to assist in positioning the distal end of the endotracheal tube within a patient. One of the most common features designed into prior art endotracheal tubes is the use of depth indicators printed on the exterior surface of the endotracheal tube. The depth indicators are indicative of the distance between the distal end of the endotracheal tube and the indicator marking itself. For example, if an orally applied endotracheal tube is advanced down a patient's throat until an indication of fifteen centimeters is seen at the patient's mouth, the person administering the endotracheal tube can see that the endotracheal tube has been advanced fifteen centimeters into the patient's mouth and into the patient's throat. By knowing the size of the patient, the person administering the endotracheal tube can estimate the proper intubation distance needed to position the distal end of the endotracheal tube within the patient's trachea.

However, even if an endotracheal tube is initially properly positioned, the position of the tube may change during the time of intubation. For example, a patient's body may be moved by a doctor during an operation. The change in the position of the body may change the position of the trachea relative the endotracheal tube, thereby causing the distal end of the endotracheal tube to leave the trachea.

Recognizing the need to retain the distal end of an endotracheal tube in the trachea during intubation, many devices have been developed in the prior art that physically anchor the endotracheal tube to the body. By anchoring the endotracheal tube to the body, it is hoped that the endotracheal tube will move with the body, thereby causing the positional relationship between the distal end of the endotracheal tube and the trachea to remain constant.

One of the most common devices used to retain an endotracheal tube in place is an endotracheal tube holder. Endotracheal tube holders, such as those exemplified by U.S. Pat. No. 5,402,776 to Islava, entitled ENDOTRACHEAL TUBE HOLDER and U.S. Pat. No. 5,345,931 to Battaglia, also entitled ENDOTRACHEAL TUBE HOLDER, show mouthpieces that strap to a patient's head. A mechanical device such as a clamp, screw or tie is then used to anchor a section of an endotracheal tube to the mouthpiece. The problems associated with such endotracheal tube holders is that they are expensive to manufacture, difficult to adjust and tend to constrict the diameter of the endotracheal tube as the endotracheal tube is anchored.

Simpler, lower cost endotracheal tube holders exist in the prior art that do not contain mouthpieces. Rather, such prior art endotracheal tube holders include a bracket that attaches directly to the endotracheal tube. The bracket provides a means by which the endotracheal tube itself can be directly strapped to a patient's head. Such endotracheal tube holders are exemplified by U.S. Pat. No. 5,398,679 to Freed, entitled HINGED ENDOTRACHEAL TUBE HOLDER HAVING BOTH A SAFETY CLAMP AND A SECURING CLAMP and U.S. Pat. No. 5,076,269 to Austin, entitled APPARATUS FOR RETENTION OF AN ENDOTRACHEAL TUBE. The disadvantage of such prior art endotracheal tube holders is that the brackets are often difficult to apply to the endotracheal tube. Furthermore, once a bracket is attached to the tube, it is very difficult to adjust the position of the bracket relative the tube.

One of the simplest prior art techniques used to anchor an endotracheal tube in place involves the use of a special strap, wherein the strap engages both the head and the endotracheal tube without the use of a mouthpiece or a bracket. Such prior art devices are exemplified by U.S. Pat. No. 5,205,832 to Truman, entitled ENDOTRACHEAL TUBE SUPPORT DEVICE and U.S. Pat. No. 4,844,061 to Carroll. In such prior art devices, the tube is coupled to the strapping either by friction (Truman patent) or adhesive (Carroll patent). With friction connections, the tube still often moves. With adhesive connections, the tube becomes glued into one position and cannot be adjusted when needed.

A need therefore exists in the prior art for an endotracheal tube holder that is low cost, simple to apply, retains the endotracheal tube firmly, is easy to adjust and does not constrict the endotracheal tube. This need is fulfilled by the present invention as described and claimed below.

SUMMARY OF THE INVENTION

The present invention is a device and associated method for retaining an endotracheal tube in a set position during the period of intubation. The device includes a tubular element that extends at least partially into the mouth of the patient being intubated. The tubular element has an interior surface upon which is affixed a first piece of hook and loop fastening material. A second piece of hook and loop fastening material is affixed to the endotracheal tube to be used during intubation. The endotracheal tube is advanced into the patient through the center of the tubular element. As the hook and loop fastening material on the endotracheal tube advances into the tubular element, an interference fit occurs between the hook and loop fastening material on the endotracheal tube and the hook and loop fastening material lining the tubular element. As the two section of hook and loop fastening material engage each other, the two sections adhere to each other, thereby connecting the endotracheal tube to the tubular element. The connection between the endotracheal tube and the tubular element is strong enough to prevent the unintentional movement of the endotracheal tube. However, the connection between the endotracheal tube and the tubular element can easily be adjusted by a medical practitioner who desires to adjust the position of the endotracheal tube. The adjustments can be made without tools and without having to remove and readminister the endotracheal tube.

BRIEF DESCRIPTION OF THE DRAWINGS

For a better understanding of the present invention, reference is made to the following description of two exemplary embodiments thereof, considered in conjunction with the accompanying drawings, in which.

DETAILED DESCRIPTION OF THE SHOWN EMBODIMENTS

Although the present invention device and method can be used to secure many types of intubation tubes, such as tracheostomy intubation tubes and nasal intubation tubes, the present invention device and method are especially well suited for use with oral intubation tubes. Accordingly, by way of example, the present invention device and method will be described in an oral intubation application.

Figure 1:
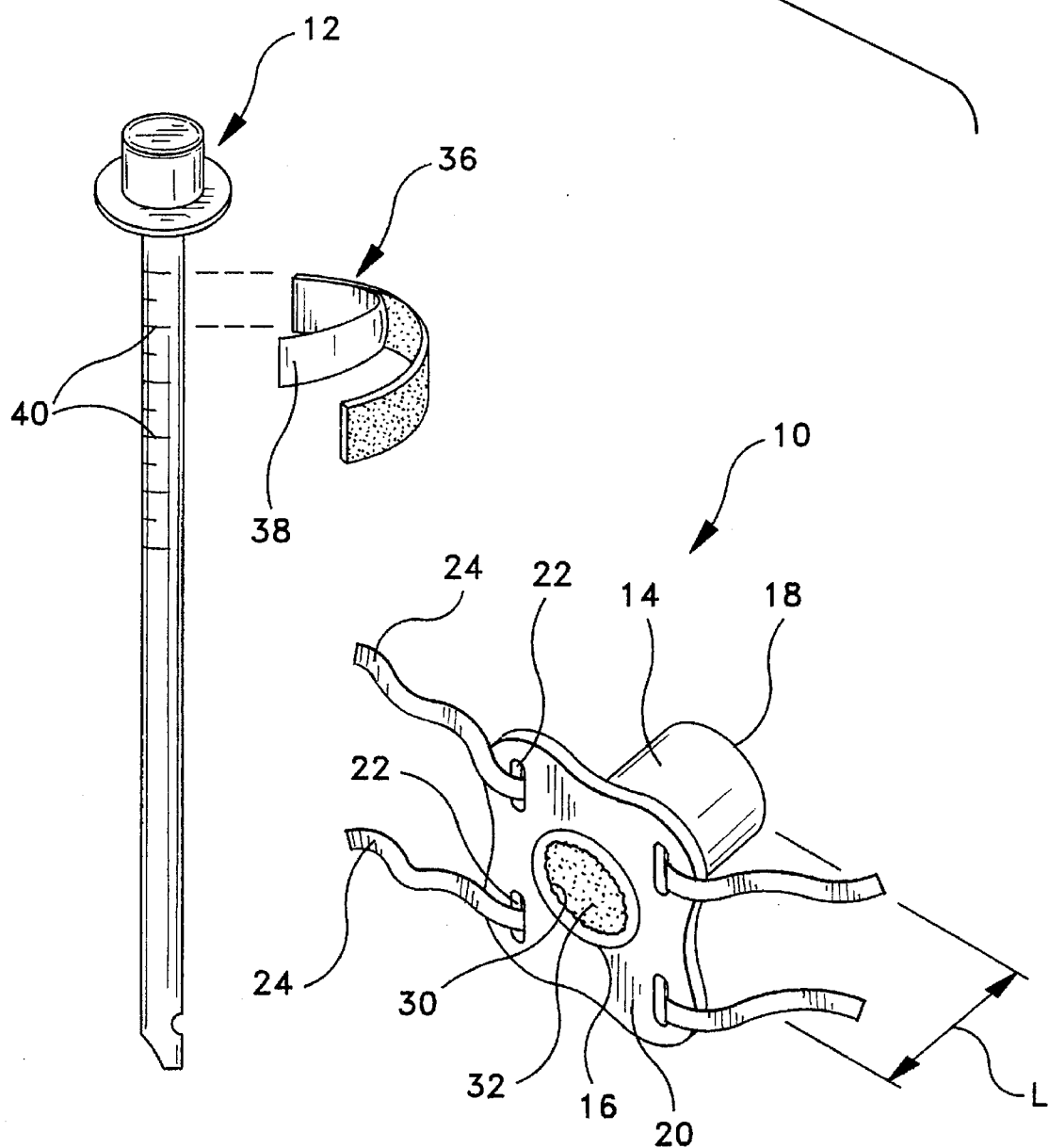
FIG. 1 shows a perspective view of a preferred embodiment of the present invention endotracheal tube holder shown in conjunction with an endotracheal tube.

Referring to FIG. 1, an exemplary embodiment of the present invention tube holder 10 is shown in conjunction with an endotracheal tube 12 used for oral intubation. The tube holder 10 includes a tubular element 14 having a first open end 16 and a second open end 18. The tubular element 14 has a length L which can be between 0.5 inches and 2.0 inches depending upon the size of the patient being intubated. A flange 20 radially extends from the tubular element 14 proximate the first open end 16. The flange 20 is sized to be larger than the mouth of the patient and therefore prevents the tubular element 14 from being inserted into a patient's mouth beyond a known distance. Strap apertures 22 are formed through the flange 20 at different points. The strap apertures 22 enable strapping 24 to be attached to the flange 20, thereby providing a means for securing the tube holder 10 to the head of the patient. In the preferred embodiment, the strapping 24 is twill tape. However, it will be understood that any known strapping used in the prior art to secure tube holders to a patient's head can also be used.

Contained within the interior of the tubular element 14 is a section of hook and loop fastening material 30 commonly sold under the brand name VELCRO®. The hook and loop fastening material 30 is adhesively affixed to the interior surface of the tubular element 14 so that the hook and loop fastening material 30 extends into the open central region 32 defined by the tubular element 14 and partially constricts the open central region 32. The hook and loop fastening material 30 can line the entire length L of the interior of the tubular element 14 or any portion thereof.

A strip of hook and loop fastening material 36 is provided to be attached to the endotracheal tube 12. The strip of hook and loop fastening material 36 has an adhesive coating on its underside that is manufactured to strongly adhere to the plastics used in the formation of endotracheal tubes. The adhesive coating is initially covered by a peel away strip 38 that protects the adhesive coating prior to its application onto the endotracheal tube 12. The endotracheal tube 12 can be most any endotracheal tube currently used in an intubation procedure. In the shown embodiment, the endotracheal tube 12 has depth gauge markings 40 on its exterior that informs the medical practitioner performing the intubation procedure how deep into the trachea the endotracheal tube is descending. The medical practitioner performing the intubation procedure knows the size of the patient and the length of the endotracheal tube 12. From this information, the medical practitioner is able to estimate the depth to which the endotracheal tube 12 must be advanced. This initial estimate may be verified by a fluoroscopic image and often the initial estimate is slightly adjusted as needed.

The strip of hook and loop fastening material 36 is applied to the endotracheal tube 12 at the point corresponding to the estimated depth at which the endotracheal tube 12 will be inserted. The strip of hook and loop fastening material 36 is preferably large enough so that the strip of hook and loop fastening material 36 can be wrapped around the endotracheal tube 12 so that the area of the endotracheal tube 12 covered by the strip of hook and loop material 36 extends approximately one half an inch on either side of the point of estimated depth. As will later be explained, the overlap enables the position of the endotracheal tube 12 to be adjusted as needed.

Figure 2:
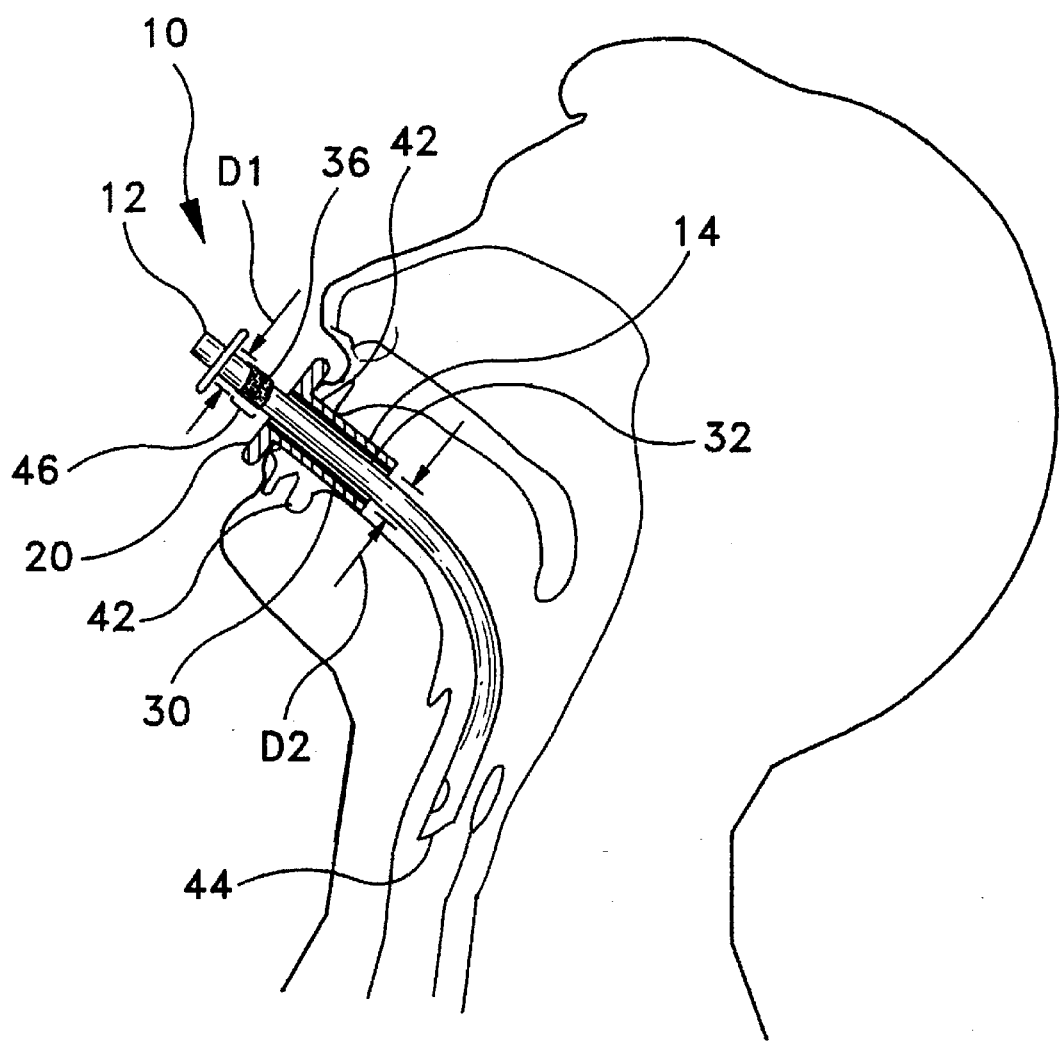
FIG. 2 shows a selectively cross-sectioned view of the endotracheal tube holder shown in FIG. 1 shown in conjunction with an endotracheal tube during use in an intubation procedure.

Referring to FIG. 2, it can be seen that the present invention tube holder 10 is placed into the mouth of a patient, so that the tubular element 14 extends into the patient. The tubular element 14 extends past the teeth 42 of the patient. As a result, the tubular element 14 is preferably made from a material that prevents the patient from collapsing the tubular element 14, should the patient bite down upon the tubular element 14 during the period of intubation. The strapping 24 (FIG. 1) retains the flange 20 in position against the face of the patient and prevents the patient from displacing the tube holder 10 with facial movements or movements of the tongue.

As the endotracheal tube 12 is inserted into the patient, the output end 44 of the endotracheal tube 12 is passed through the open central region 32 of the tube holder's tubular element 14. As the output end 44 approaches the proper position in the trachea, the region 46 of the endotracheal tube 12 containing the strip of hook and loop fastening material 36 passes into the open central region 32 of the tubular element 14. The diameter D1 of the strip of hook and loop fastening material 36 on the endotracheal tube 12 is larger than the diameter D2 of the open central region 32 lined with the hook and loop material 30. As a result, a slight interference fit occurs between the endotracheal tube 12 and the tubular element 14, wherein the hook and loop fastening material 36 on the endotracheal tube 12 engages the hook and loop fastening material 30 lining the interior of the tubular element 14. As the sections of hook and loop fastening material 30, 36 touch, the sections of hook and loop fastening material 30, 36 engage each other, thereby coupling the endotracheal tube 12 to the tube holder 10. The interconnection between the endotracheal tube 12 and the tube holder 10 is not permanent. Rather, the endotracheal tube 12 can be moved in relation to the tube holder 10 provided the endotracheal tube 12 is pushed or pulled with a force sufficient enough to overcome the forces of the hook and loop fastening material. As such, it should be understood that the position of the endotracheal tube 12 can be adjusted relative the tube holder 10 throughout the range where some portion of the strip of hook and loop fastening material 36 on the endotracheal tube 12 engages some portion of the hook and loop fastening material 30 lining the tubular element 14 in the tube holder 10.

Figure 3:
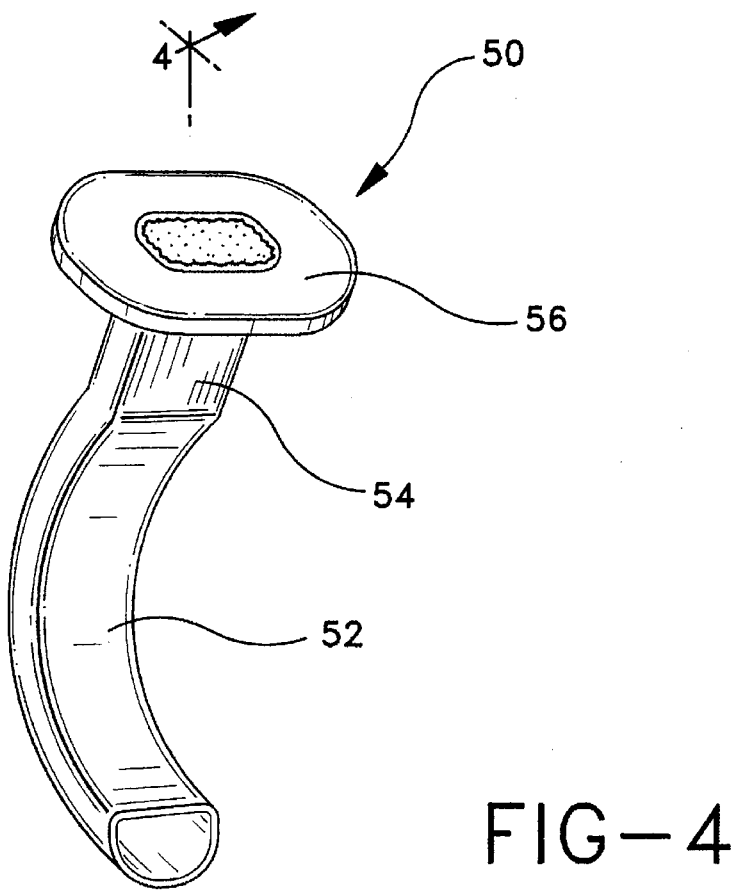
FIG. 3 shows a perspective view of the present invention endotracheal tube holder as applied to a Guedel airway.
Figure 4:
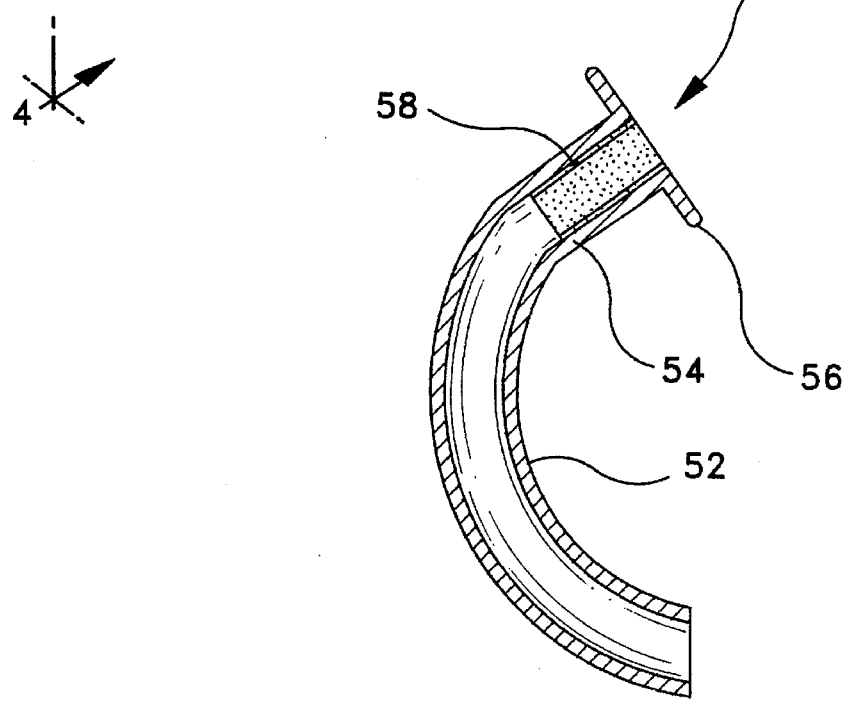
FIG. 4 shows a cross-sectional view of the embodiment of FIG. 3, viewed along section line 4—4.

Referring to FIG. 3 and FIG. 4, an intubation airway 50 is shown. Intubation airways have long been used in the prior art to help in the application and removal of intubation tubes. Intubation airways provide a curved conduit that passes over the teeth and tongue, and directs tubes passing through the conduit past the esophagus and into the trachea. In the shown embodiment, the intubation airway 50 has the general shape of a Guedel airway, wherein a curved section of conduit 52 leads into a straight section of conduit 54 and terminates at a mouthpiece flange 56. From FIG. 3 and FIG. 4, it can be seen that the straight section of conduit 54 is lined with hook and loop fastening material 58. If the endotracheal tube from FIG. 1 were inserted through the intubation airway 50, the hook and loop fastening material on the endotracheal tube would engage the hook and loop fastening material 58 the intubation airway 50. The endotracheal tube would therefore be connected to the intubation airway 50, wherein the intubation airway 50 is attached to the patient by its presence in the patient's throat.

In the embodiment of FIG. 1 and the embodiment of FIG. 3, an endotracheal tube is held in place by the interaction between two sections of hook and loop fasteners. The coupling caused by hook and loop fasteners in the embodiments is sufficient to retain the endotracheal tube in a fixed position within the trachea. As such, the relative position of the endotracheal tube within the trachea will not change should the patient move or be moved while intubated. However, the engagement between the sections of hook and loop fasteners is not permanent. As a result, with relatively little effort, a medical practitioner can adjust the position of the endotracheal tube without tools and without having to remove and reinsert the endotracheal tube.

It will be understood that the embodiments of the present invention device and method described above are merely exemplary and that many other embodiments can be produced by a person skilled in the art. For instance, many different types of endotracheal tube holders and airways exist in the prior art. Many of these prior art devices can be modified in accordance with the present invention so as to positively engage an endotracheal tube using hook and loop fasteners. All such alternate embodiments are intended to be included within the scope of the present invention as defined by the appended claims.

What is claimed is:

1. An intubation assembly, comprising:
   an endotracheal tube;
   a first piece of hook and loop fastening material coupled to a section of said endotracheal tube;
   a tubular element having an interior surface, wherein said tubular element is adapted to extend into the mouth of a patient;
   a second piece of hook and loop fastening material coupled to said interior surface of said tubular element, wherein said second piece of hook and loop fastening material engages said first piece of hook and loop fastening material when said endotracheal tube is passed into said tubular element, thereby joining said endotracheal tube to said tubular element in a predetermined positional relationship.

2. The assembly according to claim 1, further including a fastening means, coupled to said tubular element, for fastening said tubular element to a patient's head.

3. The assembly according to claim 1, wherein a flange radially extends from said tubular element, wherein said flange is sized not to fit within the mouth of the patient.

4. The assembly according to claim 3, wherein a plurality of apertures are disposed within said flange, said plurality of apertures being adapted to receive strapping therein.

5. The assembly according to claim 1, wherein said tubular element extends past the teeth in the mouth and acts as a bite block, thereby preventing the patient from biting the endotracheal tube.

6. The assembly according to claim 1, wherein said second piece of hook and loop fastening material coupled to said interior surface of said tubular element defines a restricted opening within said tubular element and said first piece of hook and loop fastening material on said section of said endotracheal tube defines a shape that creates an interference fit with said restricted opening when said endotracheal tube is placed within said tubular element.

7. An endotracheal tube holder, comprising:
   a tubular element having a first open end, an opposite second open end, an interior surface and an exterior surface;
   a flange radially extending from said exterior surface of said tubular element proximate said second open end; and
   hook and loop fastening material affixed to at least a portion of said interior surface.

8. The endotracheal tube holder according to claim 7, further including a fastening means, coupled to said tubular element, for fastening said tubular element to a patient's head.

9. The endotracheal tube holder according to claim 7, wherein a plurality of apertures are disposed within said flange, said plurality of apertures being adapted to receive strapping therein.

10. A method of securing an endotracheal tube, comprising the steps of:
    providing a tubular element having an interior surface and a first piece of hook and loop fastening material affixed to said interior surface;
    placing at least a section of said tubular element within the mouth of a patient;
    attaching a second piece of hook and loop fastening material to said endotracheal tube;
    advancing said endotracheal tube into the patient through said tubular element until said first piece of hook and loop fastening material engages said second piece of hook and loop fastening material, thereby joining said endotracheal tube to said tubular element.

11. The method according to claim 10, further including the step of securing said tubular element to the head of the patient.

12. The method according to claim 11, wherein said step of securing said tubular element includes affixing strapping to said tubular element and tying said strapping around the head of the patient.

* * * * *